(12) United States Patent
Belfadhel et al.

(10) Patent No.: US 7,547,799 B1
(45) Date of Patent: Jun. 16, 2009

(54) METHOD FOR PRODUCING PHENOLIC COMPOUND

(75) Inventors: Hatem Abdallah Belfadhel, Roosendaal (NL); Hans-Peter Brack, Herrliberg (CH); Martin Walde, Mettmenstetten (CH); Dennis James Patrick Maria Willemse, Standdaarbuiten (NL)

(73) Assignee: Sabic Innovative Plastics IP B.V., Bergen op Zoom (NL)

( * ) Notice: Subject to any disclaimer, the term of this patent is extended or adjusted under 35 U.S.C. 154(b) by 0 days.

(21) Appl. No.: 12/143,379

(22) Filed: Jun. 20, 2008

(51) Int. Cl.
*C07C 69/88* (2006.01)
(52) U.S. Cl. ....................................... 560/71
(58) Field of Classification Search ........................ None
See application file for complete search history.

(56) References Cited

U.S. PATENT DOCUMENTS

| | | | |
|---|---|---|---|
| 3,919,118 | A | 11/1975 | Robinson et al. |
| 4,094,912 | A | 6/1978 | Feinstein et al. |
| 4,206,186 | A | 6/1980 | Holter et al. |
| 4,242,195 | A | 12/1980 | Rudnick |
| 4,323,668 | A | 4/1982 | Brunelle |
| 4,324,637 | A | 4/1982 | Durai-Swamy |
| 4,324,638 | A | 4/1982 | Durai-Swamy |
| 4,324,639 | A | 4/1982 | Durai-Swamy |
| 4,324,640 | A | 4/1982 | Durai-Swamy |
| 4,324,641 | A | 4/1982 | Durai-Swamy |
| 4,324,642 | A | 4/1982 | Durai-Swamy |
| 4,324,643 | A | 4/1982 | Durai-Swamy |
| 4,324,644 | A | 4/1982 | Durai-Swamy |
| 4,480,691 | A | 11/1984 | Hoerter et al. |
| 4,731,491 | A | 3/1988 | Urban et al. |
| 5,091,591 | A | 2/1992 | Cipullo |
| 5,142,086 | A | 8/1992 | King, Jr. et al. |
| 5,151,491 | A | 9/1992 | Sakashita et al. |
| 5,189,139 | A | 2/1993 | Tuinstra et al. |
| 5,276,129 | A | 1/1994 | Sakashita et al. |
| 5,525,701 | A | 6/1996 | Tominari et al. |
| 5,696,222 | A | 12/1997 | Kaneko et al. |
| 6,177,536 | B1 | 1/2001 | Anamizu et al. |
| 6,252,036 | B1 | 6/2001 | Hatono et al. |
| 6,300,459 | B1 | 10/2001 | Kaneko et al. |
| 6,303,734 | B1 | 10/2001 | Funakoshi et al. |

(Continued)

FOREIGN PATENT DOCUMENTS

EP     0688807 B1    12/1995

(Continued)

*Primary Examiner*—Karl J Puttlitz
(74) *Attorney, Agent, or Firm*—Larson & Anderson, LLC

(57) ABSTRACT

A method is provided for producing an ester-substituted phenol product stream from an ester-substituted diaryl carbonate manufacturing waste stream. The method includes the steps of obtaining a waste stream containing an ester-substituted diaryl carbonate from an ester-substituted diaryl carbonate manufacturing facility and creating a reaction mixture by combining the waste stream with a solvent and with a transesterification catalyst. The reaction mixture is maintained at a reaction pressure at or below atmospheric pressure, and at a reaction temperature for a period of time sufficient to produce ester-substituted phenol by solvolysis of the ester-substituted diaryl carbonate. Ester-substituted phenol is removed from the reaction mixtures in an ester-substituted phenol stream. The solvent, the reaction temperature, and the reaction time are selected in combination such that less than 1,000 ppm of acid-substituted phenol is present in the ester-substituted phenol stream.

16 Claims, 11 Drawing Sheets

U.S. PATENT DOCUMENTS

| | | | |
|---|---|---|---|
| 6,399,739 B1 | 6/2002 | McCloskey et al. | |
| 6,403,754 B1 | 6/2002 | McCloskey et al. | |
| 6,410,777 B1 | 6/2002 | Kaneko et al. | |
| 6,417,291 B1 | 7/2002 | Kaneko et al. | |
| 6,420,512 B1 | 7/2002 | McCloskey et al. | |
| 6,420,588 B1 | 7/2002 | McCloskey et al. | |
| 6,469,192 B1 | 10/2002 | Burnell et al. | |
| 6,500,914 B1 | 12/2002 | Brack et al. | |
| 6,506,871 B1 | 1/2003 | Silvi et al. | |
| 6,518,391 B1 | 2/2003 | McCloskey et al. | |
| 6,525,163 B1 | 2/2003 | Brack et al. | |
| 6,548,623 B2 | 4/2003 | Brunelle et al. | |
| 6,590,068 B2 | 7/2003 | Brack et al. | |
| 6,600,004 B1 | 7/2003 | McCloskey et al. | |
| 6,653,434 B2 | 11/2003 | Brack et al. | |
| 6,703,473 B2 | 3/2004 | Hucks et al. | |
| 6,706,846 B2 | 3/2004 | Brack et al. | |
| 6,710,156 B2 | 3/2004 | Whitney et al. | |
| 6,723,823 B2 | 4/2004 | McCloskey et al. | |
| 6,734,277 B2 | 5/2004 | Brack et al. | |
| 6,747,119 B2 | 6/2004 | Brack et al. | |
| 7,066,254 B2 | 6/2006 | Vinegar et al. | |
| 7,086,465 B2 | 8/2006 | Wellington et al. | |
| 7,100,994 B2 | 9/2006 | Vinegar et al. | |
| 7,151,189 B2 * | 12/2006 | Murthy et al. | 558/270 |
| 7,339,070 B2 * | 3/2008 | Murthy et al. | 558/275 |
| 2002/0095020 A1 | 7/2002 | Hucks et al. | |
| 2002/0132957 A1 | 9/2002 | Brack et al. | |
| 2004/0068086 A1 | 4/2004 | Day et al. | |
| 2004/0087756 A1 | 5/2004 | Ramesh et al. | |
| 2005/0234211 A1 | 10/2005 | Martinez et al. | |
| 2006/0069228 A1 | 3/2006 | McCloskey et al. | |
| 2007/0119041 A1 | 5/2007 | Mascarenas et al. | |
| 2007/0135611 A1 | 6/2007 | Brack et al. | |
| 2008/0004417 A1 | 1/2008 | Jansen et al. | |
| 2008/0004418 A1 | 1/2008 | Jansen et al. | |
| 2008/0287640 A1 | 11/2008 | Belfadhel et al. | |

FOREIGN PATENT DOCUMENTS

| | | |
|---|---|---|
| JP | 4153218 | 5/1992 |
| JP | 5009282 A2 | 1/1993 |
| JP | 10101786 A2 | 4/1998 |
| JP | 10101787 A2 | 4/1998 |
| JP | 11302228 A2 | 11/1999 |
| JP | 2000129112 A | 5/2000 |
| JP | 2002309015 A2 | 10/2002 |
| WO | 8200655 A1 | 3/1982 |
| WO | 03040208 A1 | 5/2003 |
| WO | 03106149 A1 | 12/2003 |

* cited by examiner

METHOD FOR PRODUCING PHENOLIC COMPOUND

BACKGROUND

Ester-substituted diaryl carbonates, such as bismethylsalicylcarbonate, are important reactants in the production of polycarbonate resins. As the use of polycarbonate resins has increased, the efficient production of ester-substituted diaryl carbonate has become more important.

Waste streams from the ester-substituted diaryl carbonate manufacturing process require special handling for disposal. The waste streams typically comprise a variety of compounds such as ester-substituted diaryl carbonate, ester-substituted phenol, and derivatives thereof. Currently there is no economically useful process to efficiently recover these compounds from a waste stream.

As is reported in U.S. Pat. Nos. 7,339,070 and 7,151,189, processes exists for recycling waste product streams from non-ester-substituted diaryl carbonate production facilities, for example those that produce diaryl carbonates such as diphenyl carbonate (DPC). In these patents a process is disclosed where a waste product stream containing diphenyl carbonate is reacted in an alkyl alcohol, such as methanol, at high temperatures, high pressure, and high residence times to breakdown residual diphenyl carbonate into its phenolic precursor, phenol. Phenol is then separated from the balance of the components and used to form/reform diphenyl carbonate.

The present Inventors found that this process does not produce an acceptable stream of ester-substituted phenol that can be used for later reactions to form/reform ester-substituted diaryl carbonate and polycarbonate. At these high temperatures, high pressures, and high residence times, the Inventors found the ester-substituted phenol present in the reaction mixture converts to acid-substituted phenol which has been found to cause problems in down stream reaction processes that produce ester-substituted diaryl carbonate and polycarbonate from the ester-substituted diaryl carbonate. In addition, such conditions are very energy intensive and require special equipment and thus have high investment and variable costs.

As is reported in U.S. patent application Ser. No. 11/748,951, it was found that an acid-substituted phenol such as salicylic acid can lead to process instability in the melt formation of polycarbonate using the ester-substituted diaryl carbonate as a carbonate source. It is believed that the acid-substituted phenol negatively impacts the performance of the melt transesterification catalyst used in the melt polymerization process. The acid-substituted phenol is believed to have its greatest impact at the earlier lower temperature stage of the melt polymerization process, for example during the oligomerization stage.

Problems arising from the acid-substituted phenol and the generation of it are not observed in the methods described in U.S. Pat. Nos. 7,339,070 and 7,151,189 because non-ester-substituted diaryl carbonates, such as diphenyl carbonate, do not contain a degradable ester linkage that is capable of degrading to form the undesired byproduct acid-substituted phenol.

Therefore, it would be extremely desirable to find processes where a waste stream from an ester-substituted diaryl carbonate production facility can be efficiently recycled to recover reusable materials from the stream while minimizing or eliminating the formation of acid-substituted phenol in the product stream.

SUMMARY OF INVENTION

The inventors have now found a process for the efficient and effective recycling of a waste stream received from an ester-substituted diaryl carbonate production facility that minimizes and can even eliminate the formation of an acid-substituted phenol in the product ester-substituted phenol stream. In one embodiment, a method for producing an ester-substituted phenol product stream from an ester-substituted diaryl carbonate manufacturing waste stream, comprises the steps of:
(1) obtaining a waste stream from an ester-substituted diaryl carbonate manufacturing facility, the waste stream comprising an ester-substituted diaryl carbonate,
(2) creating a reaction mixture by combining the waste stream with a solvent selected from the group consisting of methanol, ethanol, n-propanol, iso-propanol and water, and with a transesterification catalyst,
(3) maintaining the reaction mixture at a reaction pressure at or below atmospheric pressure, and at a reaction temperature for a period of time sufficient to produce ester-substituted phenol by solvolysis of the ester-substituted diaryl carbonate, and
(4) removing the ester-substituted phenol in an ester-substituted phenol stream, wherein the solvent, the reaction temperature, and the reaction time are selected in combination such that less than 1,000 ppm of acid-substituted phenol is present in the ester-substituted phenol stream.

DETAILED DESCRIPTION

Figure 1:
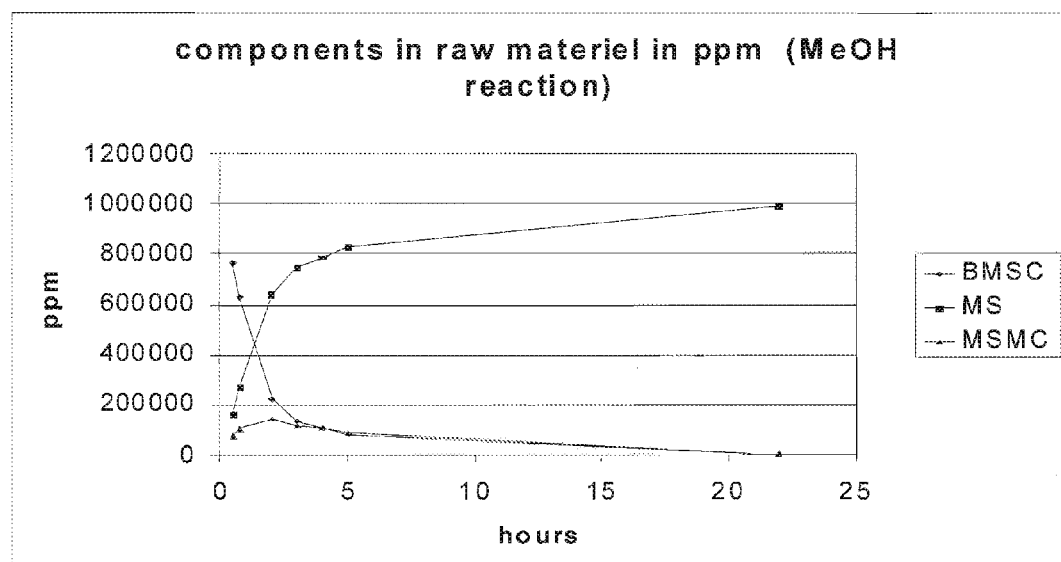
FIGS. 1 to 11 show results from the Example Section.

The inventors have now found processes for the efficient and effective recycling of a waste stream received from an ester-substituted diaryl carbonate production facility that minimizes and can eliminate the formation of an acid-substituted phenol in the product ester-substituted phenol stream. As is reported in U.S. patent application Ser. No. 11/748,951, which is incorporated herein by reference for all purposes, an acid-substituted phenol such as salicylic acid can lead to process instability in the melt formation of polycarbonate using the ester-substituted diaryl carbonate as a carbonate source. The present invention provides advantageous methods, inter alia, that can recycle waste stream from the ester-substituted diaryl carbonate facility while minimizing formation of the undesirable acid-substituted phenol.

In one embodiment, a method for producing an ester-substituted phenol product stream from an ester-substituted diaryl carbonate manufacturing waste stream, comprises the steps of:
(1) obtaining a waste stream from an ester-substituted diaryl carbonate manufacturing facility, the waste stream comprising an ester-substituted diaryl carbonate,
(2) creating a reaction mixture by combining the waste stream with a solvent selected from the group consisting of methanol, ethanol, n-propanol, iso-propanol and water, and with a transesterification catalyst, (3) maintaining the reaction mixture at reaction pressure at or below atmospheric pressure, and at a reaction temperature for a period of time sufficient to produce ester-substituted phenol by solvolysis of the ester-substituted diaryl carbonate, and (4) removing the ester-substituted phenol in an ester-substituted phenol stream, wherein the solvent, the reaction temperature, and the reaction time are selected in combination such that less than 1,000 ppm of acid-substituted phenol is present in the ester-substituted phenol stream.

Within the above defined method the Inventors have found at least two different reaction mixture formulations and corresponding process conditions that achieve solvolysis of the ester-substituted diaryl carbonate to produce an ester-substituted phenol containing less than 1,000 ppm of acid-substituted phenol. In a first of these embodiments, a batch-type process may be employed to produce an ester-substituted phenol wherein the solvent is selected from the group consisting of methanol, ethanol, n-propanol, and iso-propanol, and wherein the reaction mixture comprises less than 1,000 ppm water. In this first embodiment the solvolysis reaction occurs via alcoholysis of the ester-substituted diaryl carbonate owing to the selected solvent being an alcohol. To minimize the formation of the acid-substituted phenol it is important to limit the temperature and time that the generated ester-substituted phenol is in contact with water. This is accomplished by maintaining the reaction mixture at a reaction temperature below the boiling point of the selected solvent at the reaction pressure for a period of time sufficient to generate ester-substituted phenol by alcoholysis of the ester-substituted diaryl carbonate. During the alcoholysis reaction ester-substituted phenol concentration increases in the reaction mixture. Therefore, the presence of water in the reaction mixture should be minimized to prevent hydrolysis of the ester-substituted phenol acid-substituted phenol over the course of the alcoholysis reaction.

In a second embodiment a continuous-type or semi-continuous-type process may be employed to produce an ester-substituted phenol. In this second embodiment, the Inventors have found that the presence of water is less problematic in the reaction mixture and the reaction can occur at elevated temperature (e.g. above the boiling point of the selected solvent at the reaction pressure) owing to the fact that generated ester-substituted phenol is contiguously or semi-continuously removed from the reaction mixture to maintain its concentration at or below 1 wt. % of the reaction mixture. In fact the Inventors have found that in the present embodiment, water can suitably be used as the solvent and therefore the solvolysis reaction can occur by either or both of hydrolysis (wherein the solvent comprises water) or solvolysis (e.g. wherein the solvent comprises an alcohol). Both of these embodiment of the methods of the present invention will be further described below.

Definitions

As used in the specification and claims of this application, the following definitions, should be applied:

"a", "an", and "the" as an antecedent refer to either the singular or plural. For example, "an aromatic dihydroxy compound" refers to either a single species of compound or a mixture of such species unless the context indicates otherwise.

"Polycarbonate" refers to polycarbonates incorporating repeat units derived from at least one dihydroxy aromatic compound and includes copolyestercarbonates, for example a polycarbonate comprising repeat units derived from resorcinol, bisphenol A, and dodecandioic acid. Nothing in the description and claims of this application should be taken as limiting the polycarbonate to only one dihydroxy residue unless the context is expressly limiting. Thus, the application encompasses copolycarbonates with residues of 2, 3, 4, or more types of dihydroxy compounds. Furthermore the term "polycarbonate" includes both oligomers (e.g. polycarbonate polymers having from 2 to 40 repeat units derived from dihydroxy compound(s)) as well as higher molecular weight polymers (e.g. those having a number average molecular weight, Mn measured relative to polystyrene (PS) standards of between 10,000 g/mol and 160,000 g/mol).

"Solvolysis" as it is herein used to describe the degradation reaction of ester-substituted diaryl carbonate to ester-substituted phenol and is herein understood to mean either or both of a hydrolysis reaction and/or alcoholysis reaction that occurs between the ester-substituted diaryl carbonate and the selected solvent to form the ester-substituted phenol product. Wherein the selected solvent comprises water the solvolysis reaction will be by hydrolysis and wherein the selected solvent comprises and alcohol the solvolysis reaction will be by alcoholysis.

"Acid-substituted phenol" refers to a carboxylic acid substituted phenolic compound such as salicylic acid. The content of the acid-substituted phenol is the content as extracted by water from a pulverized samples of the ester-substituted diaryl carbonate mixture or a solution of the melt reaction mixture in dichloromethane and then analyzed by HPLC.

"Salicylic acid" is an example of an acid substituted phenol that may be contained in melt polymerization processes that uses ester-substituted diaryl carbonate (e.g. BMSC) as a carbonate source. Salicylic acid (CAS number 69-72-7) is also know as 2-Hydroxybenzoic acid and o-hydroxybenzoic acid and has chemical formula $C_7H_6O_3$ (e.g. HO—$C_5H_4$—COOH). Salicylic acid has the structure as depicted in FIG. 1 and below:

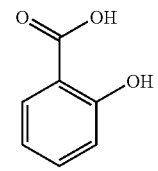

"ppm" for example when used as "ppm acid-substituted phenol" is herein understood to mean parts per million. For example 10 ppm acid-substituted phenol in ester-substituted phenol or melt reaction mixture is 10 milligrams acid-substituted phenol per kg ester-substituted diaryl carbonate or per kilogram melt reaction mixture, respectively. The acid-substituted phenol concentrations and levels referred to in the specification are those as measured by the HPLC method as described below.

Numerical values in the specification and claims of this application, particularly as they relate to polymer compositions, reflect average values for a composition that may contain individual polymers of different characteristics. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

Materials

A. Ester-substituted Diaryl Carbonate

The waste stream obtained from an ester-substituted diaryl carbonate manufacturing facility will comprise an ester-substituted diaryl carbonate. In a preferred embodiment to ensure plain efficiencies, the waste stream will comprise an amount of ester-substituted diaryl carbonate that is worth recovering. These ester-substituted diaryl carbonates will preferably have the structure,

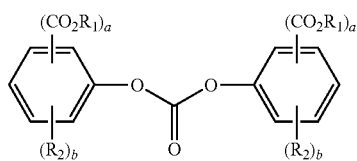

wherein $R^1$ is independently at each occurrence a $C_1$-$C_{20}$ alkyl radical, $C_4$-$C_{20}$ cycloalkyl radical, or $C_4$-$C_{20}$ aromatic radical; $R^2$ is independently at each occurrence a halogen atom, cyano group, nitro group, $C_1$-$C_{20}$ alkyl radical, $C_4$-$C_{20}$ cycloalkyl radical, $C_4$-$C_{20}$ aromatic radical, $C_1$-$C_{20}$ alkoxy radical, $C_4$-$C_{20}$ cycloalkoxy radical, $C_4$-$C_{20}$ aryloxy radical, $C_1$-$C_{20}$ alkylthio radical, $C_4$-$C_{20}$ cycloalkylthio radical, $C_4$-$C_{20}$ arylthio radical, $C_1$-$C_{20}$ alkylsulfinyl radical, $C_4$-$C_{20}$ cycloalkylsulfinyl radical, $C_4$-$C_{20}$ arylsulfinyl radical, $C_1$-$C_{20}$ alkylsulfonyl radical, $C_4$-$C_{20}$ cycloalkylsulfonyl radical, $C_4$-$C_{20}$ arylsulfonyl radical, $C_1$-$C_{20}$ alkoxycarbonyl radical, $C_4$-$C_{20}$ cycloalkoxycarbonyl radical, $C_4$-$C_{20}$ aryloxycarbonyl radical, $C_2$-$C_{60}$ alkylamino radical, $C_6$-$C_{60}$ cycloalkylamino radical, $C_5$-$C_{60}$ arylamino radical, $C_1$-$C_{40}$ alkylaminocarbonyl radical, $C_4$-$C_{40}$ cycloalkylaminocarbonyl radical, $C_4$-$C_{40}$ arylaminocarbonyl radical, or $C_1$-$C_{20}$ acylamino radical; a is an integer between 1 and 3 inclusive; b is an integer between 0 and 4 inclusive; and the sum of a and b for each aromatic group is less than or equal to 5.

In a preferred embodiment the ester-substituted diaryl carbonate is an activated ester-substituted diaryl carbonate. One method for determining whether a certain ester-substituted diaryl carbonate is activated or is not activated is to carry out a model transesterification reaction between the certain diaryl carbonate with a phenol such as p-(1,1,3,3-tetramethyl)butylphenol. This phenol is preferred because it possesses only one reactive site, possesses a low of volatility and possesses a similar reactivity to bisphenol-A. The model transesterification reaction is carried out at temperatures above the melting points of the certain ester-substituted diaryl carbonate and p-(1,1,3,3-tetramethyl)butylphenol and in the presence of a transesterification catalyst, which is usually an aqueous solution of sodium hydroxide or sodium phenoxide. Preferred concentrations of the transesterification catalyst are about 0.001 mole % based on the number of moles of the phenol or diaryl carbonate. A preferred reaction temperature is 200° C. The choice of conditions and catalyst concentration can be adjusted depending on the reactivity of the reactants and melting points of the reactants to provide a convenient reaction rate. The only limitation to reaction temperature is that the temperature must be below the degradation temperature of the reactants. Sealed tubes can be used if the reaction temperatures cause the reactants to volatilize and affect the reactant molar balance. The determination of the equilibrium concentration of reactants is accomplished through reaction sampling during the course of the reaction and then analysis of the reaction mixture using a well-known detection method to those skilled in the art such as HPLC (high pressure liquid chromatography). Particular care needs to be taken so that reaction does not continue after the sample has been removed from the reaction vessel. This is accomplished by cooling down the sample in an ice bath and by employing a reaction quenching acid such as acetic acid in the water phase of the HPLC solvent system. It may also be desirable to introduce a reaction quenching acid directly into the reaction sample in addition to cooling the reaction mixture. A preferred concentration for the acetic acid in the water phase of the HPLC solvent system is 0.05% (v/v). The equilibrium constant was determined from the concentration of the reactants and product when equilibrium is reached. Equilibrium is assumed to have been reached when the concentration of components in the reaction mixture reach a point of little or no change on sampling of the reaction mixture. The equilibrium constant can be determined from the concentration of the reactants and products at equilibrium by methods well known to those skilled in the art. An ester-substituted diaryl carbonate which possesses a relative equilibrium constant ($K_{test}/K_{DPC}$) of greater than 1 is considered to possess a more favorable equilibrium than diphenylcarbonate and is an activated ester-substituted diaryl carbonate, whereas an ester-substituted diaryl carbonate which possesses an equilibrium constant of 1 or less is considered to possess the same or a less favorable equilibrium than diphenylcarbonate and is considered not to be an activated ester-substituted diaryl carbonate. It is generally preferred to employ an activated ester-substituted diaryl carbonate with very high reactivity compared to diphenylcarbonate when conducting transesterification reactions. Preferred are activated ester-substituted diaryl carbonates with an equilibrium constant greater than at least 10 times that of diphenylcarbonate.

In certain embodiments the electron-withdrawing group(s) are at ortho and/or para positions relative to the carbonate substituent on the aromatic group. For example wherein the electron-withdrawing group is an ortho ester-substituted.

Examples of preferred activated ester-substituted diaryl carbonates suitable for use with the present invention include bismethylsalicylcarbonate (CAS Registry No. 82091-12-1), bisethylsalicylcarbonate, bispropylsalicylcarbonate, bisbutylsalicylcarbonate, bisbenzylsalicyl carbonate, bismethyl 4-chlorosalicyl carbonate and the like. Typically bismethylsalicylcarbonate is preferred for use in melt polycarbonate synthesis due to its lower molecular weight and higher vapor pressure.

B. Ester-Substituted Phenol

As the solvolysis reaction proceeds ester-substituted diaryl carbonate is degraded into its components to form ester-substituted phenol. The structure of the generated ester-substituted phenol will depend on what type of ester-substituted diaryl carbonate is present in the waste stream. For example, if bismethylsalicylcarbonate (BMSC) is present in the waste stream, a typical ester-substituted phenol will be methyl salicylate.

In general, the ester-substituted phenol has the structure,

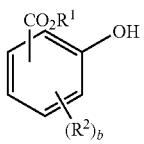

wherein $R^1$ is a $C_1$-$C_{20}$ alkyl group, $C_4$-$C_{20}$ cycloalkyl group, or $C_4$-$C_{20}$ aryl group; $R^2$ is independently at each occurrence a halogen atom, cyano group, nitro group, $C_1$-$C_{20}$ alkyl group, $C_4$-$C_{20}$ cycloalkyl group, $C_4$-$C_{20}$ aryl group, $C_1$-$C_{20}$ alkoxy group, $C_4$-$C_{20}$ cycloalkoxy group, $C_4$-$C_{20}$ aryloxy group, $C_1$-$C_{20}$ alkylthio group, $C_4$-$C_{20}$ cycloalkylthio group, $C_4$-$C_{20}$ arylthio group, $C_1$-$C_{20}$ alkylsulfinyl group, $C_4$-$C_{20}$ cycloalkylsulfinyl group, $C_4$-$C_{20}$ arylsulfinyl group, $C_1$-$C_{20}$ alkylsulfonyl group, $C_4$-$C_{20}$ cycloalkylsulfonyl group, $C_4$-$C_{20}$ arylsulfonyl group, $C_1$-$C_{20}$ alkoxycarbonyl group, $C_4$-$C_{20}$ cycloalkoxycarbonyl group, $C_4$-$C_{20}$ aryloxycarbonyl group, $C_2$-$C_{60}$ alkylamino group, $C_6$-$C_{60}$ cycloalkylamino group, $C_5$-$C_{60}$ arylamino group, $C_1$-$C_{40}$ alkylaminocarbonyl group, $C_4$-$C_{40}$ cycloalkylaminocarbonyl group, $C_4$-$C_{40}$ arylaminocarbonyl group, or $C_1$-$C_{20}$ acylamino group; and b is an integer 0-4.

Examples of suitable ester-substituted phenols include methyl salicylate, ethyl salicylate, propyl salicylate, butyl salicylate, 4-chloro methyl salicylate, n-propyl salicylate, benzyl salicylate and mixtures thereof. Typically, methyl salicylate is preferred as BMSC is frequently preferred as a carbonate source for melt polycarbonate production.

C. Acid-substituted Phenol

The acid-substituted phenol in this invention refers to a carboxylic acid substituted phenolic compound. In one embodiment the acid-substituted phenol has the structure:

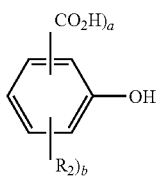

where a, $R_2$, and b have been described above with regard to the ester-substituted diaryl carbonate. In one embodiment the acid-substituted phenol is an ortho substituted phenol.

These acidic impurities include and are not limited to salicylic acid (CAS #69-72-7), 4-hydroxybenzoic acid (CAS #99-96-7), 3-fluoro-4-hydroxybenzoic acid (CAS #350-29-8), 4-Hydroxyisophthalic acid (CAS #636-46-4), 4-Hydroxy-3-nitrobenzoic acid (CAS #616-82-0), 5-Methylsalicylic acid (CAS #89-56-5), 4-Methylsalicylic acid (CAS #50-85-1), 3-Methylsalicylic acid (CAS #83-40-9), 5-Fluorosalicylic acid (CAS #345-16-4), 3-Chlorosalicylic acid (CAS #1929-32-9), 5-Chlorosalicylic acid (CAS #321-14-2), 2-Hydroxy-5-nitrobenzoic acid (CAS #96-97-9), 3-Nitrosalicylic acid (CAS #85-38-1).

Without being bound by a particular mechanism, the inventors believe that the acid-substituted phenol may be formed by the following two-step reaction mechanism, especially at elevated temperatures:

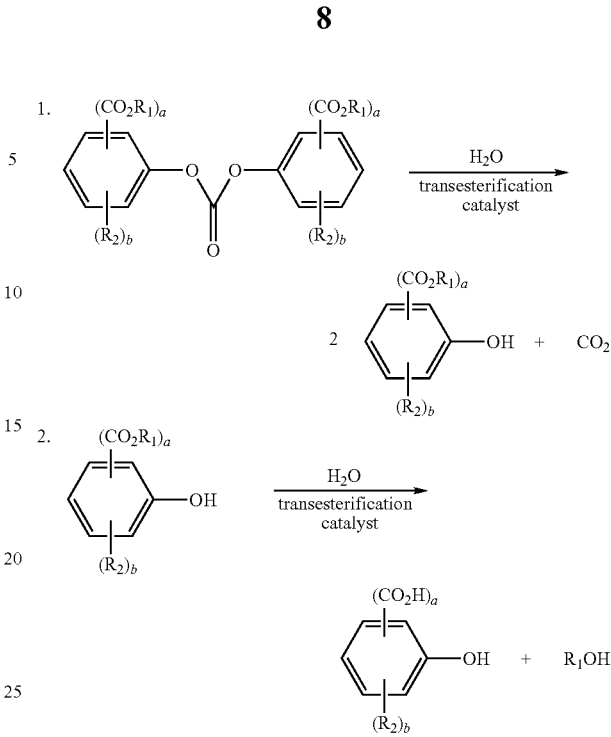

It is believed that these hydrolysis reactions that form the carboxylic acid substituted phenolic compound may proceed even at ambient temperatures, albeit more slowly than would occur at elevated temperatures. It is believed that these hydrolysis reactions proceed quite rapidly though either in solution or in melt at temperatures above the melting point of the ester-substituted diaryl carbonate (for example above about 110° C. where the ester-substituted diaryl carbonate is BMSC).

As described above, in a preferred embodiment for the production of polycarbonate the ester-substituted diaryl carbonate is bismethylsalicylcarbonate (BMSC). BMSC may be hydrolyzed to yield methyl salicylate and finally salicylic acid according to the following reaction scheme:

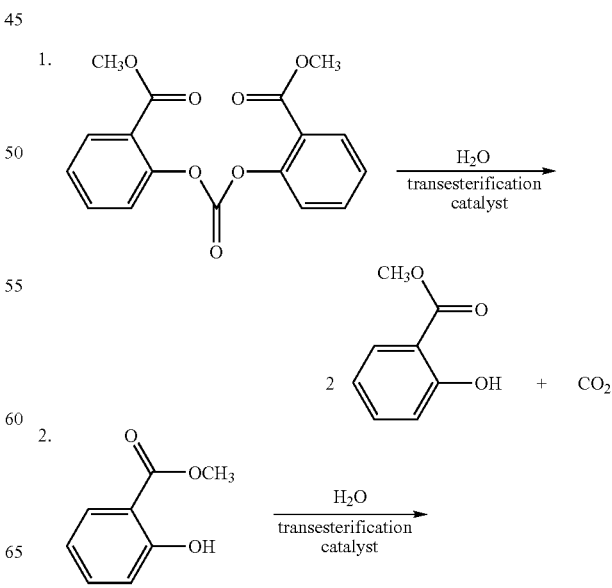

-continued

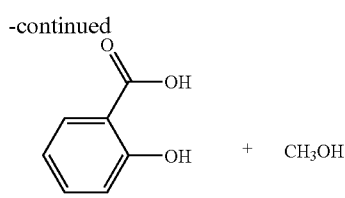 + CH₃OH

D. Solvent

The method of the invention comprises the step of combining the waste stream and a transesterification catalyst with a solvent. As described above, the present invention provides two embodiments for practicing the method of the present invention. In both embodiments the term "solvent" means that an effective amount of the solvent is employed/present in the reaction mixture to cause a solvolysis reaction of the ester-substituted diaryl carbonate to form ester-substituted diaryl carbonate. Therefore, in some embodiments a large amount of solvent is present to ensure that the reaction component is dissolved in the solvent whereas in other embodiments a minimal amount of solvent is present to ensure that a solvolysis reaction can occur at the given reaction conditions. Solvolysis is a type of nucleophilic substitution or elimination where the nucleophile is a solvent molecule. For certain nucleophiles, there are specific terms for the type of solvolysis reaction. In the present invention, for water the term is hydrolysis and for alcohols, it is alcoholysis.

In the first embodiment (batch-type process) of the method described herein the components of the waste stream and catalyst may be partially or completely dissolved in a low molecular weight alcohol solvent (e.g. low molecular alkyl alcohols those having less than 10 carbon atoms). The solvolysis reaction in this first embodiment occurs by alcoholysis of the ester-substituted diaryl carbonate. Water is not a suitable solvent and it is preferred that the reaction mixture comprises less than 1,000 ppm water (e.g. more preferably less than 500 ppm, less than 100 ppm, and most preferably no water) to minimize hydrolysis of the formed ester-substituted phenol into acid-substituted phenol. It has been found that due to separation concerns in downstream processes that it is preferred that the alcohol solvent of this first embodiment is selected such that it has an atmospheric boiling point equal to or less than water to aid in the case of separating the solvent from the ester-substituted phenol and balance of components in the reaction mixture. It is preferred that in this first embodiment that the solvent is selected from the group consisting of methanol, ethanol, n-propanol, and iso-propanol.

In the second embodiment (continuous-type or semi-continuous-type process) of the method of the present invention described herein the presence of water is less problematic due to the fact that generated ester-substituted phenol is removed from the reaction mixture and therefore the ester-substituted phenol does not substantially hydrolyze to form the undesired acid-substituted phenol byproduct. Therefore, solvents that are suitable for use this second embodiment are the protic alcohol solvents described above, water, or a combination thereof. In this second embodiment it is preferred that the solvent be introduced in small amounts to molten reaction components to create a solvolysis reaction which can be controlled to produce and remove ester-substituted phenol from the reaction mixture.

The selected solvent is dependent upon the conditions under which the reaction occurs. As described, water readily hydrolyzes ester-substituted phenol into acid-substituted phenol. In the first embodiment, the solvolysis reaction (alcoholysis reaction) is run under batch-type conditions where the presence of water in the reaction mixture is minimized, to reduce its hydrolyzing impact on the formed ester-substituted phenol. In the second embodiment where ester-substituted phenol is continuously (e.g. semi-continuously) removed from the reaction mixture, water can suitably be used as a solvent, in that ester-substituted phenol is removed prior to hydrolyzation with water to form acid-substituted phenol.

E. Melt Transesterification Catalysts

The methods of the invention also comprise the step of combining a melt transesterification catalyst to the reactants to form a reaction mixture. The melt transesterification catalyst may be introduced continuously, or may be introduced batchwise and may occur before, during or after the introduction of the solvent or the ester-substituted carbonate to the reaction mixture.

The melt transesterification catalyst used in the method of the present invention is a base, and preferably comprises at least one source of alkaline earth ions or alkali metal ions, and/or at least one quaternary ammonium compound, a quaternary phosphonium compound or a mixture thereof. The source of alkaline earth ions or alkali metal ions being used in an amount such that the amount of alkaline earth or alkali metal ions present in the metal reaction mixture is in a range between about $10^{-5}$ and about $10^{-8}$ moles alkaline earth or alkali metal ion per mole of ester-substituted diaryl carbonate present in the reaction mixture.

The quaternary ammonium compound is selected from the group of organic ammonium compounds having the structure

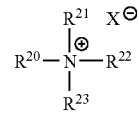

wherein $R^{20}$-$R^{23}$ are independently a $C_1$-$C_{20}$ alkyl radical, $C_4$-$C_{20}$ cycloalkyl radical, or a $C_4$-$C_{20}$ aryl radical; and $X^-$ is an organic or inorganic anion. In one embodiment of the present invention anion $X^-$ is selected from the group consisting of hydroxide, halide, carboxylate, sulfonate, sulfate, formate, carbonate, and bicarbonate.

Non-limiting examples of suitable organic ammonium compounds are tetramethyl ammonium hydroxide, tetrabutyl ammonium hydroxide, tetramethyl ammonium acetate, tetramethyl ammonium formate and tetrabutyl ammonium acetate. Tetramethyl ammonium hydroxide is often preferred.

The quaternary phosphonium compound is selected from the group of organic phosphonium compounds having the structure:

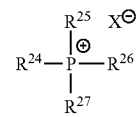

wherein $R^{24}$-$R^{27}$ are independently a $C^1$-$C^{20}$ alkyl radical, $C^4$-$C^{20}$ cycloalkyl radical, or a $C_4$-$C_{20}$ aryl radical; and $X^-$ is an organic or inorganic anion. In one embodiment of the present invention anion $X^-$ is an anion selected from the group consisting of hydroxide, halide, carboxylate, sulfonate, sulfate, formate, carbonate, and bicarbonate. Suitable organic phosphonium compounds are illustrated by tetramethyl phosphonium hydroxide, tetramethyl phosphonium acetate, tetramethyl phosphonium formate, tetrabutyl phosphonium hydroxide, and tetrabutyl phosphonium acetate (TBPA). TBPA is often preferred.

Where $X^-$ is a polyvalent anion such as carbonate or sulfate it is understood that the positive and negative charges in the above structures are properly balanced. For example, where $R^{20}$-$R^{23}$ are each methyl groups and $X^-$ is carbonate, it is understood that $X^-$ represents ½ ($CO_3^{-2}$).

Suitable sources of alkaline earth ions include alkaline earth hydroxides such as magnesium hydroxide and calcium hydroxide. Suitable sources of alkali metal ions include the alkali metal hydroxides illustrated by lithium hydroxide, sodium hydroxide and potassium hydroxide. Other sources of alkaline earth and alkali metal ions include salts of carboxylic acids, such as sodium acetate and derivatives of ethylene diamine tetraacetic acid (EDTA) such as EDTA tetrasodium salt, and EDTA magnesium disodium salt. Sodium hydroxide is often preferred as it is relatively inexpensive and used in downstream processes.

In order to achieve the sufficient solvolysis reaction of ester-substituted diaryl carbonate using the methods of the present invention an effective amount of melt transesterification catalyst must be employed. The amount of melt transesterification catalyst employed is typically based upon the total number of moles of the ester-substituted diaryl carbonate in the reaction mixture. Furthermore, the appropriate catalyst loading will depend on the temperature and reaction time. Lower reaction temperatures and shorter times will require higher catalyst loadings. Also weaker and thermally-unstable organic bases will typically require higher concentrations. Unnecessarily high catalyst loadings are believed to increase the risk of byproduct formation. Catalyst loadings of 1 to 10,000 µEq catalyst per carbonate unit are acceptable, 10-1,000 µEq catalyst per carbonate unit are preferred, and 100-600 µEq catalyst per carbonate unit are more preferred. If thermally stable non-volatile bases are used in the solution-phase method, they can likely be charged only once as they will likely stay in solution. Deactivation of catalyst or loss through degradation of devolatization will require repeat chargings to be made.

In the second embodiment (e.g. continuous-type melt phase alcoholysis or hydrolysis process), inorganic basic catalyst will stay in the melt while organic catalyst may decompose or devolatize with the solvent and ester-substituted phenol. In one embodiment, caustic (NaOH) is bubbled through the melt by injecting it into the bottom of the melted reaction components. After catalyst has been added solvent (e.g. water) can be added by injecting it into the bottom of the melted reaction components. Deactivation of catalyst or loss through degradation of devolatization will require repeat chargings to be made.

The Embodiments of the Method of the Invention

A method for producing an ester-substituted phenol product stream from an ester-substituted diaryl carbonate manufacturing waste stream is provided. The method comprises a first step of obtaining a waste stream from an ester-substituted diaryl carbonate manufacturing facility. This waste stream comprises an ester-substituted diaryl carbonate, preferably in an amount that is economically useful to treat to recover ester-substituted phenol from. In one embodiment the waste stream will comprise greater than 20 wt. % ester-substituted diaryl carbonate, more preferably greater than 50 wt. %, for example greater than 75 wt. %, like greater 90 wt % ester-substituted diaryl carbonate.

The waste stream may further comprise other compounds that are capable of reacting to form ester-substituted phenol in accordance with the reaction conditions employed in the methods of the present invention. A waste stream from a diaryl carbonate production facility producing an ester-substituted diaryl carbonate such as bismethylsalicylcarbonate (BMSC) will typically comprise compounds listed in Table 1.

In a next step, the waste stream is combined with a solvent selected from the group consisting of methanol, ethanol, n-propanol, iso-propanol, and water, and with a transesterification catalyst. As will be described below the selected solvent will be chosen in combination with the reaction conditions to minimize the formation of acid-substituted phenol present in the ester-substituted phenol produced. The reaction mixture is maintained at a reaction pressure at or below atmospheric pressure and at a reaction temperature for a period of time sufficient to produce ester-substituted phenol by solvolysis of the ester-substituted diaryl carbonate.

Ester-substituted phenol is then removed in an ester-substituted phenol stream from the reaction components. The selected solvent, the reaction time, and reaction temperature are

TABLE 1

Compounds in a waste stream from a BMSC production facility

Salicylic Acid

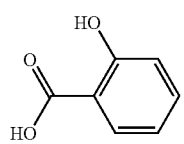

Methyl Ether of MS

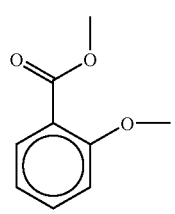

TABLE 1-continued
Compounds in a waste stream from a BMSC production facility
Methyl Carbonate of MS 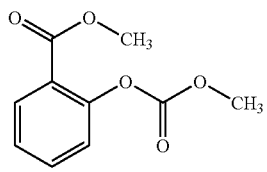
Methyl Salicylate 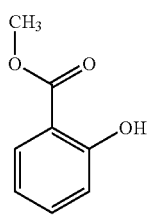
Diëthyl Carbamate of MS 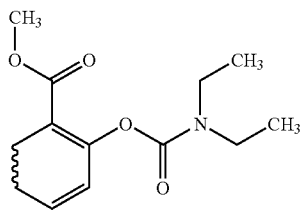
BMS-Ether 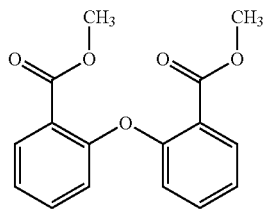
BMSC 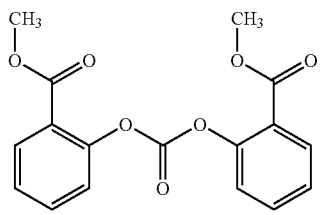
Methyl Salicyl Phenyl Carbonate (MSPC) 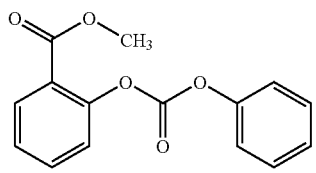
Methyl Ester-Substituted BMSC 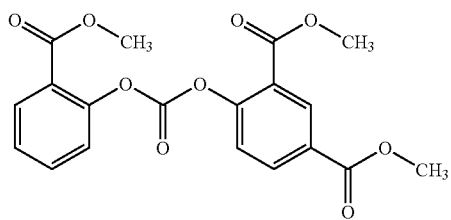

TABLE 1-continued

Compounds in a waste stream from a BMSC production facility

Methyl-Substituted BMSC

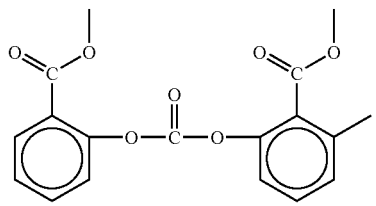

Trimer of MS ether

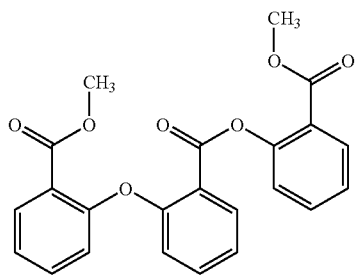

Trimer of BMSC

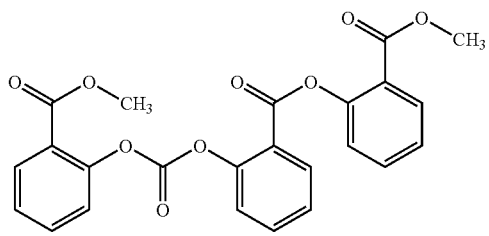

selected in combination such that less than 1,000 ppm, more preferably less than 100 ppm, and most preferably less than 10 ppm of acid-substituted phenol in the ester-substituted phenol stream.

The variables of the selected solvent, the reaction time and reaction temperature are related to and can be altered to minimize the formation of acid-substituted phenol. In general the formation of acid-substituted phenol occurs over time when ester-substituted phenol is in the presence of water at high temperatures. As described herein and within the above defined method the present Inventors have found at least two different reaction mixture configurations and corresponding process conditions that achieve solvolysis of the ester-substituted diaryl carbonate to produce an ester-substituted phenol containing less than 1,000 ppm of acid-substituted phenol I. The First Embodiment "A Batch-type Process"

In a first of these embodiments, a batch-type process may be employed to produce an ester-substituted phenol wherein the solvent is selected from the group consisting of methanol, ethanol, n-propanol, and iso-propanol, and wherein the reaction mixture comprises less than 1,000 ppm water (e.g. more preferably less than 500 ppm, less than 100 ppm, and most preferably no water). The phrase "batch-type process" is herein understood to mean that the ester-substituted phenol produced by the reaction between the solvent and the ester-substituted phenol is not continuously removed from the reaction mixture as it is produced. Instead the concentration of the ester-substituted phenol is allowed to increase within the reaction mixture as the reaction proceeds.

In this first embodiment the solvolysis reaction occurs via alcoholysis of the ester-substituted diaryl carbonate owing to the selected solvent being an alcohol. To minimize the formation of the acid-substituted phenol it is important to limit the temperature and time that the generated ester-substituted phenol is in contact with water. This is accomplished by minimizing water in the reaction mixture and maintaining the reaction mixture at a reaction temperature below the boiling point of the selected solvent at the reaction pressure for a period of time sufficient to generate ester-substituted phenol by alcoholysis of the ester-substituted diaryl carbonate.

During the alcoholysis reaction of this first batch-type process embodiment the ester-substituted phenol concentration increases in the reaction mixture as the alcoholysis reaction goes toward higher conversion. Therefore, the presence of water in the reaction mixture should be minimized while minimizing the reaction temperature to prevent hydrolysis of the ester-substituted phenol acid-substituted phenol over the course of the alcoholysis reaction.

As indicated, water is not an acceptable solvent for the present batch-type embodiment. The reaction mixture may however contain water that is present as a residual in the either the waste stream, the alcohol solvent, and/or from a catalyst addition stream, inter alia. Therefore, in a preferred practice these components and/or the reaction mixture itself are preferably 'dried' prior to initiating the alcoholysis reaction of the reaction mixture.

The selection of the reaction temperature will affect the alcoholysis reaction to form ester-substituted phenol from ester-substituted diaryl carbonate. It will also affect the hydrolysis reaction of the product ester-substituted phenol with water to form acid-substituted phenol. In the present embodiment the Inventors have found that the reaction temperature should be below the atmospheric boiling point of the selected solvent, and more preferably at a temperature less than the boiling point of the solvent at the reaction pressure. It is noted that the lower the selected temperature, the longer the solvolysis reaction will need to occur to achieve desired conversion. Therefore, the low end of the temperature range should be preferably high enough to maintain the solvolysis reaction at a rate to produce ester-substituted phenol in meaningful amounts.

Subject to the provisos above, the reaction temperature is preferably maintained in a range of at or between 40° C. and the boiling point of the solvent at the selected reaction pressure. For example in a range of between 40° C. and 80° C., like between 50° C. and 70° C. In one embodiment the reaction can take place for a period of time (e.g. the reaction time) of more than 1 hour for example between 2 and 24 hours, or longer. The present inventors have found the solvolysis reaction preferably occurs at a pressure of up to atmospheric pressure, and more preferably at less than atmospheric pressure (e.g. less than 0.8 bar).

It is preferable to have a sufficient amount solvent present to initiate and maintain the nucleophilic substitution "solvolysis" reaction. In one embodiment the solvent is present in the reaction mixture in an amount sufficient to partially dissolve, and more preferably completely dissolve, the reaction components in the reaction mixture. It is noted that a waste stream obtained from a diaryl carbonate production facility may not be very soluble in the alcohol solvents of the present embodiment and it is estimated to have a solubility of near one wt. % up to 15-20 wt %, depending on temperature. Furthermore two moles of alcohol per carbonate linkage are theoretically required for full conversion of ester-substituted diaryl carbonate into ester-substituted. Lastly, high amounts of alcohol solvent help suppress the hydrolysis reaction of MS to form SA and alcohol. However, excessively high alcohol contents will be less economically efficient because of the need to remove and recycle the alcohol from the ester-substituted phenol prior to reacting to form, or reform, ester-substituted diaryl carbonate in downstream processes.

II. The Second Embodiment "A Continuous-Type Process" and/or "A Semi-Continuous-Type Process"

In a second embodiment, a continuous-type or semi-continuous-type process may be employed to produce an ester-substituted phenol. The phrases "continuous-type process" and "semi-continuous-type process" are herein understood to mean that produced ester-substituted phenol is removed from the reaction mixture after it has been generated. This can be done at all times (e.g. continuously) or it can be done periodically (e.g. semi-continuously). In either case it is most preferred that product ester-substituted phenol is removed from the reaction mixture to maintain an amount product ester-substituted phenol in the reaction mixture such that it makes up 1.0 wt. % or less, for example 0.5 wt. % or less, and most preferably 0.25 wt. % wt. % or less of the reaction mixture.

In this second embodiment, the Inventors have found that the presence of water in the reaction mixture is less problematic and the reaction can occur at elevated temperature (e.g. above the boiling point of the selected solvent at the reaction pressure) owing to the fact that generated ester-substituted phenol is removed from the reaction mixture such that it makes up 1.0 wt. % or less of the reaction mixture. In fact the Inventors have found that in the present embodiment, water can suitably be used as a solvent and therefore the solvolysis reaction can occur by either or both of hydrolysis (e.g. wherein the solvent comprises water) or alcoholysis (e.g. wherein the solvent comprises an alcohol) or both hydrolysis and alcoholysis (e.g. wherein the solvent comprises both water and alcohol).

As is described in U.S. patent application Ser. No. 11/748, 951, which is incorporated herein by reference for all purposes, ester-substituted diaryl carbonate (e.g. BMSC) and ester-substituted phenol (e.g. MS) degrade to form acid-substituted phenol (e.g. Salicylic Acid SA). In order to minimize risk of hydrolysis of ester-substituted phenol to acid-substituted phenol, it is important to have a low concentration of water whenever MS is present. Therefore in the present embodiment the inventors have found that small amounts of solvent (e.g. water) can be introduced (e.g. bubbled) to and through the reaction components thereby forming the reaction mixture. This can be accomplished by melting melting the waste stream and the catalyst and by injecting water or water vapor into the melt while removing water and formed ester-substituted phenol from the surface of the melt. It has been found, however, that by using an alcohol instead of water helps minimize the degradation risk of the formed ester-substituted diaryl carbonate.

During the solvolysis reaction the reaction mixture is preferably tested to determine the concentration of ester-substituted phenol and to determine whether the rate of removal of the ester-substituted phenol should be increased or could be decreased. In another embodiment, the acid-substituted phenol concentration of the product ester-substituted phenol stream is measured to determine whether the rate of removal of the ester-substituted phenol should be increased or could be decreased.

In the present embodiment, due to the controlled presence of the ester-substituted phenol in the reaction mixture, the reaction temperature can be considerably higher and more adverse than in the batch-type process described above since less ester-substituted phenol is present for potential degradation. To aid in the continuous removal of ester-substituted phenol from the reaction mixture, the reaction mixture is maintained at a reaction temperature at or above the boiling point of the selected solvent at the reaction pressure for a sufficient period of time to produce ester-substituted phenol from the ester-substituted diaryl carbonate. In this embodiment, ester-substituted phenol is removed in gaseous form with gaseous solvent. The ester-substituted product stream is then preferably treated in a subsequent treatment step to remove solvent from the product ester-substituted phenol. In a preferred embodiment the reaction mixture is maintained at a reaction temperature between 100° C. and 220° C., more preferably between 120° C. and 215° C., and most preferably between 130° C. and 210° C.

To help drive off formed ester substituted phenol from the reaction mixture the inventors have found that low pressure should be employed. The present inventors have found the solvolysis reaction preferably occurs at a pressure of up to atmospheric pressure, and more preferably at less than atmospheric pressure (e.g. less than 0.8 bar), and most preferably less than 0.7 bar.

EXAMPLES

Having described the invention in detail, the following examples are provided. The examples should not be considered as limiting the scope of the invention, but merely as illustrative and representative thereof.

(I) Laboratory Experiments

The following laboratory experiments were performed to provide a fundamental understanding of which conditions enable bismethylsalicylcarbonate (BMSC) to react to form methyl salicylate (MS). In all examples acid-treated and rinsed glassware was used to avoid contamination by surface ions. In these studies all reactions were done in a 500 or 250 ml round bottom flask with a metallic stirrer and a stirrer motor. The initial principle was to use relatively harsh reaction conditions in order to determine if BMSC was capable of reacting to form MS. After it was determined that this was possible, the next step was to determine mild reaction conditions to allow the formation of MS from BMSC. All analyses on the final material from each test were done using a HPLC with a UV detector.

Chemicals and Compositions Used:
BMSC
BMSC "Lights" tar composition (Distillate 1): Composition shown in the following table 2.
BMSC "Heavies" tar composition (Distillate 2): Composition shown in the following table 3.
Sodium hydroxide (NaOH) solution 0.1M
TMAH solution 25%
Methanol (HPLC quality)
Dichloromethane (PA)

TABLE 2

Typical BMSC "Lights" tar composition (Distillate 1. % is mass percent)

| Lights removal tar composition | | average | Stdev |
|---|---|---|---|
| Salicylic acid | (%) | 0.03 | 0.07 |
| Methyl ether of MS | (%) | 0.05 | 0.06 |
| Methyl carbonate of MS [A] | (%) | 2.03 | 0.52 |
| Methyl salicylate | (%) | 1.58 | 2.37 |
| Diëthyl carbamaat of MS | (%) | 0.67 | 0.12 |
| BMSc Ether | (%) | 0.03 | 0.04 |
| BMSC | (%) | 94.96 | 2.44 |
| Methyl salicyl phenyl carbonate (MSPC) | (%) | 0.58 | 0.22 |
| BMSC methyl ester [C] | (%) | 0.00 | 0.00 |
| BMSC methyl [D] | (%) | 0.01 | 0.00 |
| Trimer of MS ether | (%) | 0.00 | 0.01 |
| Trimer | (%) | 0.04 | 0.01 |
| Other unknowns | (%) | 0.05 | 0.21 |
| MeCl2 | ppm | 14.05 | 8.69 |
| APHA | (Hazen) | 16.75 | 3.37 |

TABLE 3

Typical "Heavies" tar composition (Distillate 2, % in mass percent):

| Heavies removal Tar quality | | average | Stdev |
|---|---|---|---|
| Salicylic acid | (%) | 0.00 | 0.00 |
| Methyl ether of MS | (%) | 0.00 | 0.00 |
| Methyl carbonate of MS | (%) | 0.02 | 0.00 |
| Methyl salicylate | (%) | 0.06 | 0.06 |
| Diethyl carbamaat of MS | (%) | 0.00 | 0.00 |
| BMSC Ether | (%) | 0.00 | 0.00 |
| BMSC | (%) | 90.33 | 1.25 |
| Methyl salicyl phenyl carbonate (MSPC) | (%) | 0.01 | 0.00 |
| BMSC methyl ester | (%) | 0.01 | 0.01 |
| BMSC methyl | (%) | 0.02 | 0.00 |
| Trimer of MS ether | (%) | 1.12 | 0.99 |
| Trimer | (%) | 7.60 | 0.54 |
| Other unknowns | (%) | 0.84 | 0.11 |
| MeCl2 | ppm | 0.33 | 0.18 |
| APHA | (Hazen) | 973.20 | 98.12 |
| Fe | (ppm) | 0.08 | 0.01 |

Determination of the Solubility of BMSC in MeOH at 65° C. (with Reflux):

BMSC was loaded in a round bottom flask, a small amount of MeOH was added to the BMSC, to form a slurry. This mixture was heated up to 65° C. under reflux. MeOH was then continuously added under vigorous stirring, until a lucid and colorless solution was obtained. This test resulted in a 5.8 mass % of BMSC in MeOH solution.

Reactions in Methanol Solutions:

These reactions were performed to minimize/avoid the formation of salicylic acid. With an excess of MeOH during the reaction, the equilibrium between the formation of salicylic acid and methyl salicylate is shifted to the side of methyl salicylate. 200 μl of catalyst was added to the saturated solution of BMSC in methanol at 65° C. The oil bath was set at 85° C. and the reaction mixture was left to react under reflux and vigorous stirring for over 20 hours.

The different approaches for this test are summarized in the following table 4

TABLE 4

| | Experiment 1 | Experiment 2 | Experiment 3 | Experiment 4 |
|---|---|---|---|---|
| BMSC | 19.92 g | — | 80.16 g | 20.23 g |
| Residual dest1 | — | 6.052 | — | — |
| Residual dest2 | — | 13.051 | — | — |
| Methanol | 410 ml | 400 ml | 98 ml | 500 ml |
| DCM | — | — | 120 ml | — |
| Catalyst | 250 μeq TMAH + 100 μeq NaOH | 250 μeq TMAH + 100 μeq NaOH | 250 μeq TMAH + 100 μeq NaOH | 10 eq NaOH |
| T oilbath | 85° C. | 80° C. | 55° C. | 85° |
| T mixture | 65° C. | 65° C. | 40° C. | 65° |
| Reaction time | 22 h | 20.3 h | 23 h | 46.5 h |
| Distillation | Yes | yes | No | No |
| Sample time | 30 min; 45 min; 2, 3, 4, 5 & 22 hrs | 0 min, 25 min, 1, 2, 2:45 & 20:25 hrs | 0, 2, 4 & 23 hrs | 0, 1, 3, 5, 6:30, 23 27, 27:30, 46:30 hrs |

Melt Mixing Reactions:

Addition of high amounts of solvent is unwanted in a commercial plant design because of the large volumes of solvent needed and the extraction step, which is time and energy consuming. For this reason the following tests were conducted without the usage of solvents.

BMSC was added in a round bottom flask and heated up until it was molten. Because the catalyst is water based and the melting temperature of BMSC is well above 100° C., the catalyst was added under the liquid level of the reaction mixture to prevent the catalyst from stripping off upon contact with the molten BMSC. For these tests several catalyst concentrations have been used. In some cases it was tried to strip off MS by distillation to shift the reaction equilibrium to full conversion. The reaction times in this test vary up to 20 hrs or more. See Table 5 below.

(II). Examples of Methods

Example 1

Recycling of BMSC Dissolved in Methanol at 65° C. with Catalyst

Reaction:

The reaction was done using a 500 ml round bottom flask with a cooler and a magnetic stirrer attached. 19.920 g BMSC was loaded in the reactor and dissolved in 410 ml methanol at 65° C. When all BMSC was dissolved, 200 µl catalyst (250 eq TMAH+100 eq NaOH) was added to the solution. The reaction mixture was left to react under reflux for 22 hrs and subsequently cooled down to RT. Samples were taken after 30 min., 45 min., 2, 3, 4, 5, and 22 hrs.

TABLE 5

|  | Experiment 1 | Experiment 2 | Experiment 3 | Experiment 4 |
| --- | --- | --- | --- | --- |
| Water | — | 17 ml | 50 ml | — |
| Pressure | 1000-8 mbar | 1000-33 mbar | atmospheric | atmospheric |
| Continuous distillation | Yes | Yes | No | No |
| Catalyst | 250 µeq TMAH + 100 µeq NaOH | 250 µeq TMAH + 100 µeq NaOH | 250 µeq TMAH + 100 µeq NaOH | 1506 µeq NaOH |
| T oilbath | 150° C.-165° C. | 160° C. | 135° C. | 130° C. |
| T mixture | 130° C.-148° C. | — | — | — |
| Reaction time | 4.3 hrs | 2 hrs | 5:45 hrs | 26 hrs |
| BMSC | — | — | 79.89 g | 78.96 g |
| Residual dist 1 | 13 g | 26.20 g | — | — |
| Residual dist 2 | 26 g | 61.90 g | — | — |
| Sample times | During distillation according to overhead temp. | During distillation according to overhead temp. | 0, 2:25, 2:45, 3:45, 4:45, 5:45 hrs | 0, 1, 2, 3, 21, 21:45, 22:25, 25.8 hrs |

Characterization of Samples

The levels of methyl salicylate and other S-byproducts were measured by means HPLC using a UV detector (e.g. Agilent 110 Series with UV detector).

Method:

Description: Reversed Phase-Liquid Chromatography with UV Detection RP-LC-UV

Column: ODS-3 5 um 4.6×150 mm

Flow: 1.200 ml/min

Stop time: 28 min

Inject volume: 10 l

Max pressure: 20 bar

Min pressure: 5 bar

Solvent A: water+0.1% TFA

Solvent B: MeCN

Solvent C: $H_2O$

Solvent D: THF

TABLE 6

|  | Time | % B | % C | % D | Flow |
| --- | --- | --- | --- | --- | --- |
| 1 | 0.83 | 5.0 | 0.0 | 0.0 | 1.200 |
| 2 | 15.00 | 95.2 | 0.0 | 0.0 | 1.200 |
| 3 | 15.83 | 95.0 | 0.0 | 0.0 | 1.200 |
| 4 | 17.50 | 0.0 | 0.0 | 95.0 | 1.200 |
| 5 | 21.67 | 0.0 | 0.0 | 95.0 | 1.200 |
| 6 | 23.33 | 5.0 | 0.0 | 0.0 | 1.200 |

HPLC results of each of the fractions described above can be found in FIG. 1. MSMC is MS-Methyl carbonate. Full or nearly full conversion was achieved. The BMSC concentration decreased over time while the concentration of MS increased to almost 100%. The reaction of MS to MSMC is apparently reversible because the MSMC concentration dropped to nearly zero after 22 hrs.

Distillation:

A distillation was carried out on the obtained mixture after 22 hrs of reaction in the 500 ml round bottom flask which was attached to a Vigreux column, cooler, with stirrer, spider vacuum pump, regulation valve and cooling trap. The reaction mixture was kept at atmospheric pressure and was carefully heated up to 65° C. (oil bath set to 80° C.). As soon as the solution starts to boil the oil bath is set to 83° C. and the distillation starts (fraction 1). When the overhead temperature increases and stabilizes at 65° C. the second fraction is collected. In order to accelerate the distillation the oil bath temperature is increased to 88° C., the overhead temperature remained stable at 65° C. The distillation was stable for a long time and resulted in fraction 3 and 4. When the distillation slowed down, the oil bath was increased to 94° C. This however did not help significantly (fraction 5). For this reason the vacuum distillation was started by carefully decreasing the pressure to 200 mbar, the reaction mixture starts to boil briefly. In order to obtain a stable distillation again the temperature and pressure were optimized at a pressure of 9 mbar and a oil bath temperature of 131° C. When the overhead temperature was stable again fraction 6 could be collected.

Example 2

BMSC Melt Mixing with Catalyst

The reaction was done using a 250 ml round bottom flask, with cooler, vacuum pump, cooling trap and spider attached. 13 g of distillate 1 and 26 g of distillate 2 of BMSC residual was molten in the round bottom flask at 130° C. (oil bath 150° C.). When all BMSC was molten 200 µl catalyst (250 eq TMAH+100 eq NaOH) was added (under liquid level). Reaction blend was left to react for 30 minutes. The vacuum pump was turned on and the pressure decreased to 23 mbar, this resulting in boiling of the blend. Subsequently the oil bath temperature was increased to 160° C. and the pressure decreased to 16 mbar. When the overhead temperature starts to increase the first fraction could be collected. After 10 minutes the distillation is slowing down rapidly and after 30 minutes the reaction almost stopped, even when the oil bath temperature was increased to 165° C. the distillation still stopped therefore the test was stopped. Only a very small amount of distillate was obtained (2 ml, 2.318 g) as is shown in the Table 7 below:

TABLE 7

| Fraction 1 | 0.603 g |
|---|---|
| Fraction 2 | 1.715 g |
| Total | 2.318 g |

(Concentration MS very close to 100%)
Conversion: 6.45% (Assumed that BMSC distillate is 100% BMSC and distillation is ideal)

Figure 2:
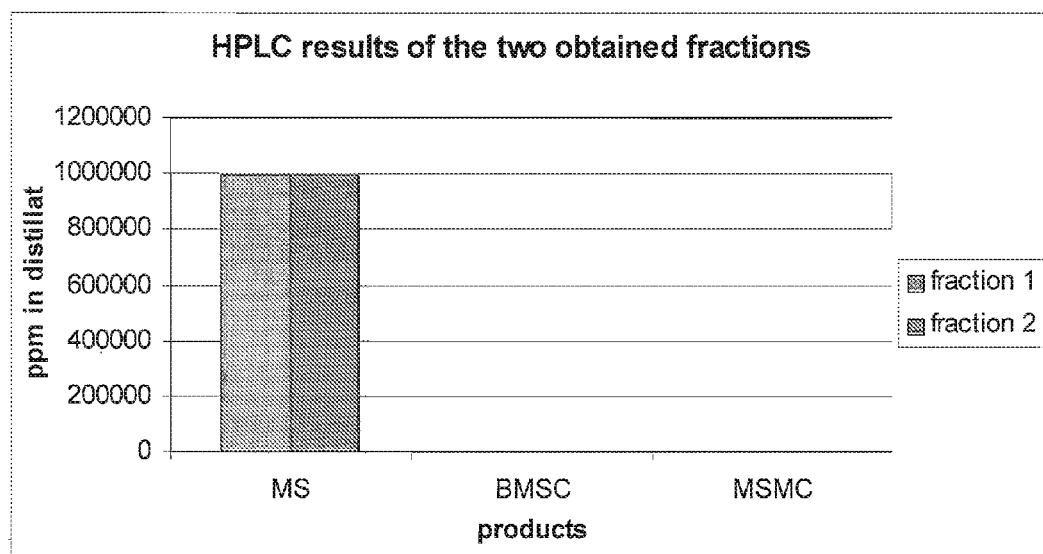

Without being bound by a particular mechanism the Inventors hypothesize the reason for low conversion was that a too low an amount of water was present during the reaction to effect complete hydrolysis. HPLC results for fractions one and two can be found in FIG. 2. The distillates are shown to be pretty clean. The only exception is in the first fraction where a small amount of MSMC was found.

Example 3

BMSC Melt Mix, Continuously Adding Water, with Catalyst and During Reaction Continuous Distillation of MS and Water The reaction was done using a 250 ml round bottom flask, with cooler, vacuum pump, cooling trap, spider, dropping funnel and a needle attached. 26.208 g of distillate 1 of BMSC and 61.90 g of distillate 2 of BMSC residual were molten in the round bottom flask at a temperature of 130° C. (oil bath 160° C.). When the mixture is completely molten 200 µl catalyst (250 eq TMAH+100 eq NaOH) is added (under the liquid level). The vacuum pump was turned on and the pressure was decreased to 200 mbar, this causes the blend to boil heavily and a lot of foam was formed. When the foam disappeared the vacuum was increased to 58 mbar. This started the distillation and fraction 1 could be collected. When the overhead temperature was stable at 62° C. fraction 2 could be obtained. After 25 minutes the distillation became slower, at this point the continuous addition of water was started. The addition point of the water was under the liquid level and was done very slowly (fraction 3). Water vaporized explosively. Much of the molten BMSC splashed all over the round bottom flask. When the overhead temperature increased to 68° C. and became stable fraction 4 was taken. After 45 minutes distillation with continuously adding of water the reaction was stopped because of a malfunction of the vacuum pump. In total 17 ml water was added. The distillate was fairly pure MS as can be seen in the Table 8 below:

TABLE 8

|  | Distillat | Concentration MS | Amount MS |
|---|---|---|---|
| Fraction 1 | 3.088 | 98.8 | 3.051 |
| Fraction 2 | 2.216 | 99.2 | 2.198 |
| Fraction 3 | 4.564 | 98.4 | 4.49 |
| Fraction 4 | 14.502 | 96.8 | 14.038 |
| total |  |  | 23.778 g |

Conversion: 29.29% (Assumed that BMSC distillate is 100% BMSC and distillation is ideal).

Figure 3:
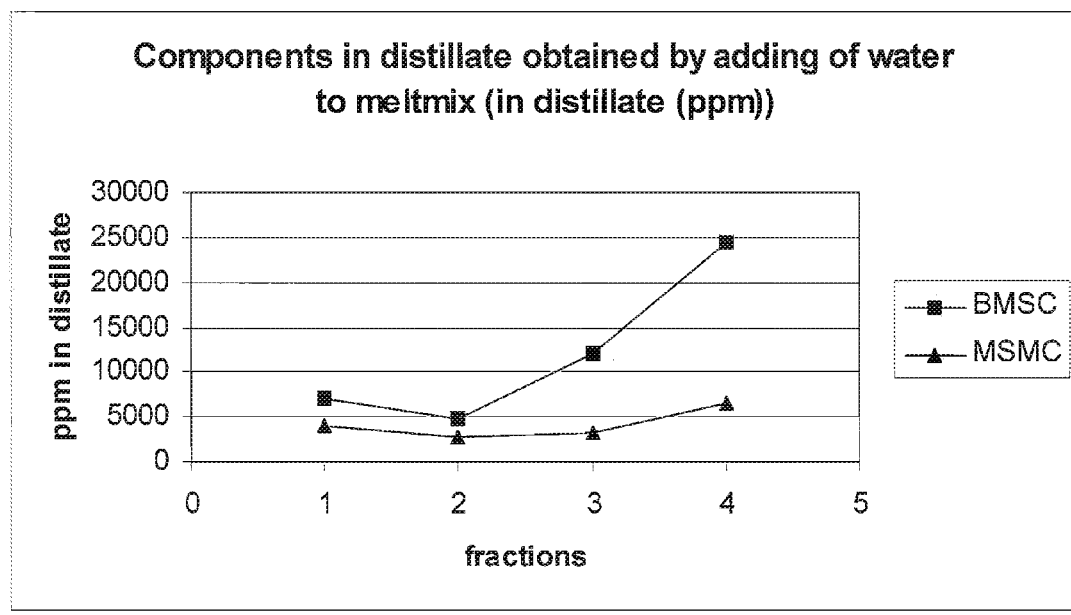
Figure 4:
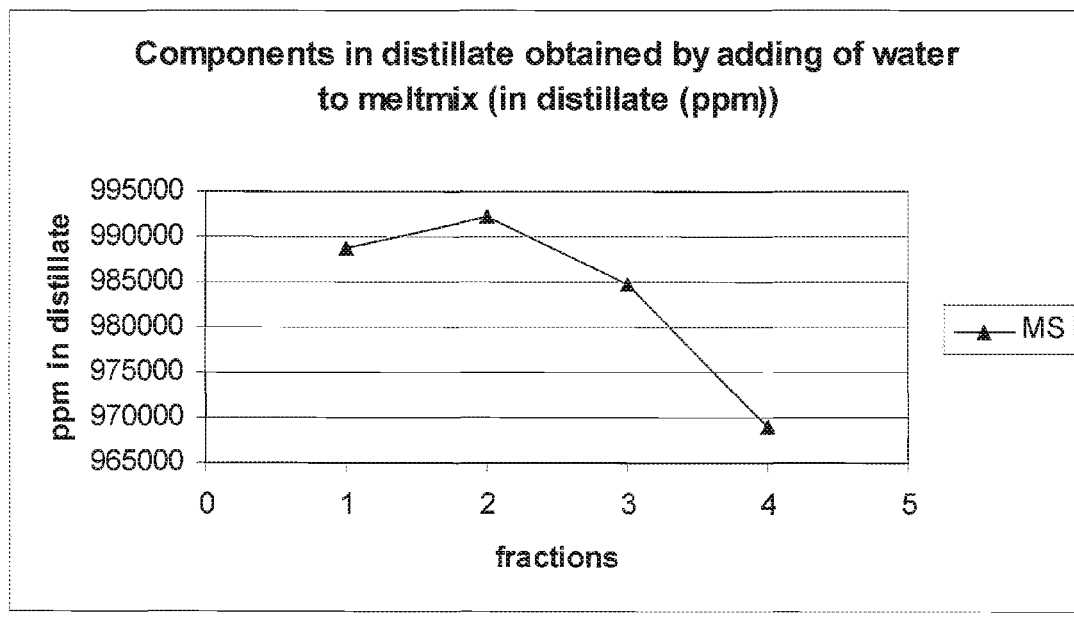

HPLC results can be found in FIGS. 3 and 4. From the results it can be concluded that when water is added continuously the formation of MSMC is increased and more BMSC is being distilled over together with the MS and the MSMC.

Example 4

Figure 5:
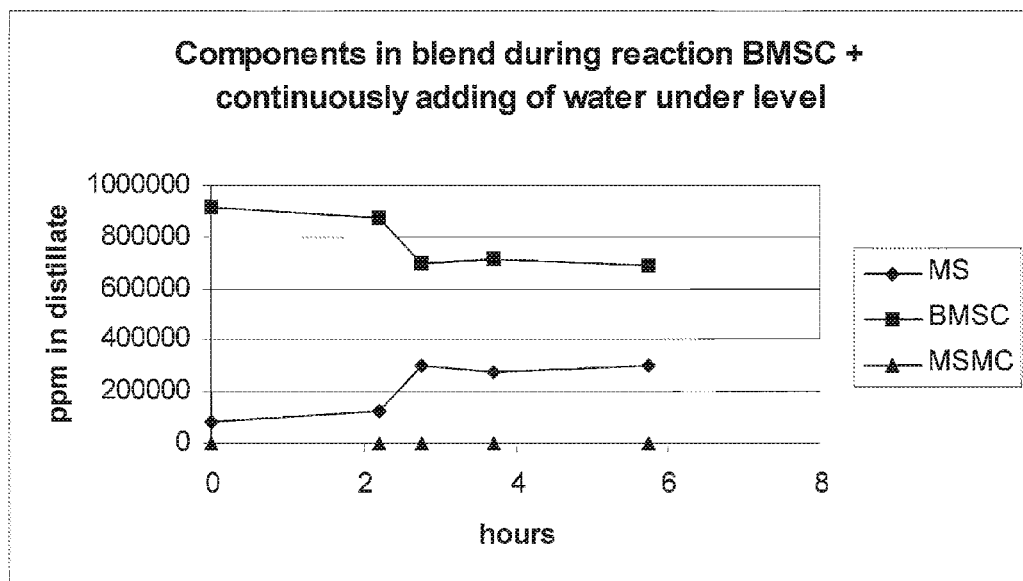

BMSC Melt Mix, Continuously Adding of Water, with Catalyst at Atmospheric Pressure Without Distillation Reaction:
The reaction was done using a 250 ml round bottom flask, with cooler, vacuum pump, cooling trap, spider, dropping funnel and needle attached. 79.89 g BMSC was loaded into the reactor and molten at temperature of 130° C. (oil bath at 160° C.). When the BMSC was completely molten 200 µl catalyst (250 eq TMAH+100 eq NaOH) was added (under the liquid level). When the catalyst was added the continuous addition of water was started (under liquid level). In total 50 ml of water was added over a time period of 4:25 hrs. Samples were taken after 0, 2:25, 2:45, 3:45, 4:45 and 5:45 hrs. HPLC results of these samples can be found in FIG. 5.

This reaction performed well initially but after 2:45 hrs the reaction apparently reached equilibrium.

Example 5

Recycling of BMSC Tar Dissolved in MeOH Using a Catalyst

Figure 6:
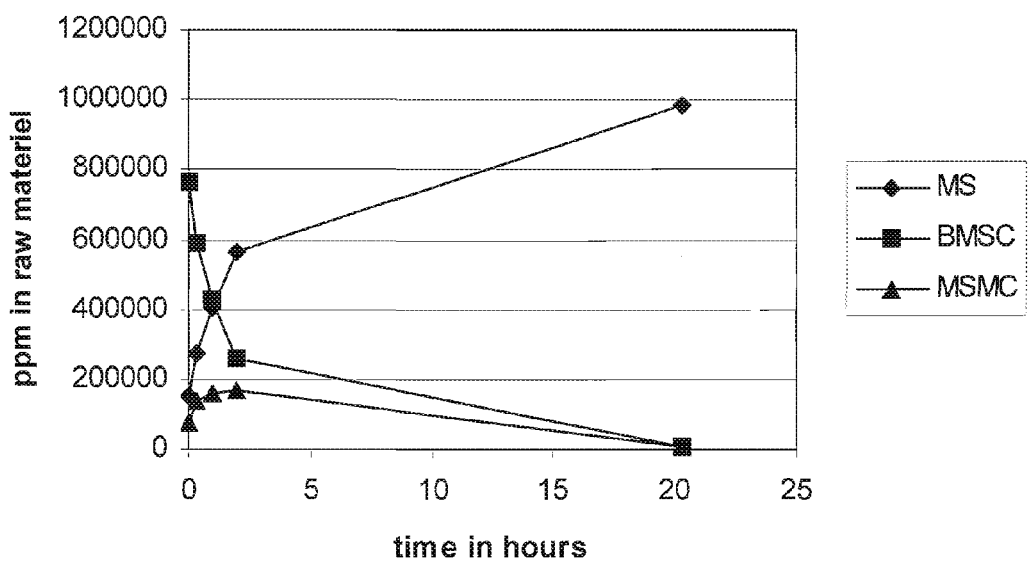

Reaction:
The reaction was done using a 500 ml round bottom flask with cooler and stirrer attached. 13.051 g residue 2 (outlined in the table 9 below) of BMSC heavies and 6.052 g residue 1 (outlined in the table 9 below) of BMSC heavies were dissolved in 400 ml methanol at 65° C. (oil bath at 80° C.) (for typical analytical values on organic purity see the table below). When all the BMSC was dissolved, 200 µl catalyst (250 equ TMAH+100 equ NaOH) was added to the solution. This reaction mixture was left to react under reflux for 20.25 hrs and afterwards cooled down to RT. Samples were taken after 0, 0:25, 1, 2, 2.7, 20.25 hrs. HPLC results for these samples are depicted in FIG. 6. The residual BMSC went to near or full conversion. Also the degradation of MSMC went toward formation of MS.

TABLE 9

|  | Unit | Residue 1 | Residue 2 |
|---|---|---|---|
| Salicylic acid | (%) | 0.00 | 0.00 |
| Methyl Ether of MS | (%) | 0.00 | 0.00 |
| Methyl Carbonate of MS | (%) | 0.06 | 0.02 |
| Methyl Salicylate | (%) | 0.03 | 0.06 |
| Diethyl Carbamate of MS | (%) | 0.00 | 0.00 |
| BMSC Ether | (%) | 0.00 | 0.00 |
| BMSC | (%) | 99.61 | 90.33 |
| Methyl Salicyl Phenyl Carbonate | (%) | 0.18 | 0.01 |
| BMSC Methyl Ester | (%) | 0.04 | 0.01 |
| BMSC Methyl | (%) | 0.03 | 0.02 |
| Trimer of MS Ether | (%) | 0.00 | 1.12 |
| Trimer | (%) | 0.04 | 7.60 |
| Unknowns | (%) | 0.00 | 0.84 |

Example 6

Melt Mixing of BMSC, Continuous Addition of 0.1M NaOH

Reaction:

The reaction was done using a 500 ml round bottom flask with cooler, stirrer, dropping funnel and a needle attached. 78.96 g BMSC was loaded into the reactor and heated (oil bath at 130° C.). When the BMSC was molten the very slow continuous addition of 0.1M NaOH was started (under liquid level). Samples were taken after 0, 1, 3, 20 hrs. After 20 hrs there was just 3 ml of the caustic solution added although plug valve completely open, apparently the NaOH solution was to viscus. For this reason 0.6 ml 0.1M NaOH was added under level with a syringe and the mixture was then left to react for other 5 hrs. Samples were taken at: 20:45, 21:25 and 25 hrs. (Ratio catalyst to BMSC: 1505.9 eq).

Figure 7:
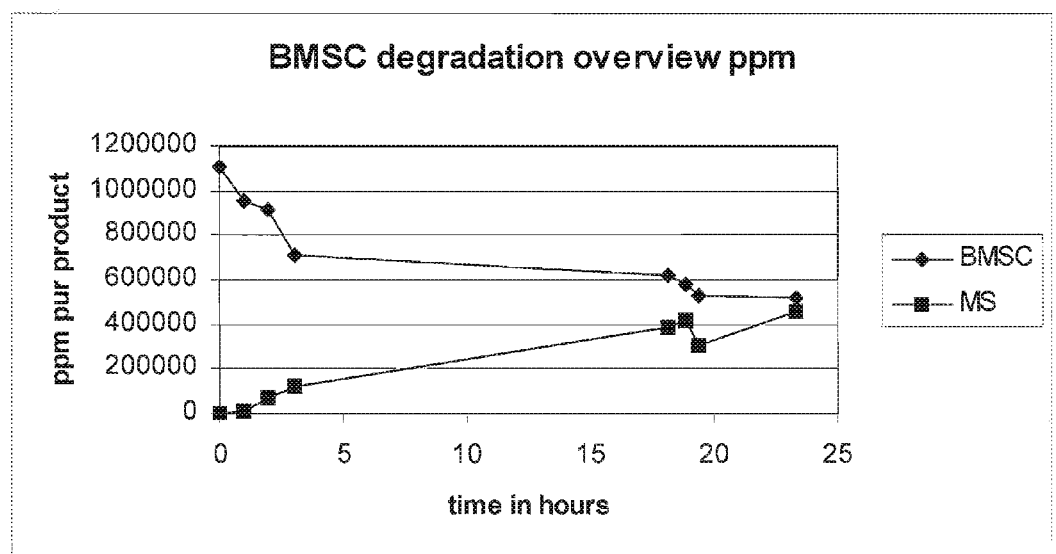

HPLC results of these samples can be found in FIG. 7. From this graph it can be concluded that the reaction had reached an equilibrium. It was then decided to remove the MS formed in the reaction by distillation, to push the reaction towards completion.

Distillation:

A distillation was carried out on roughly 20.6 g of the remaining reaction blend in a 250 ml round bottom flask with stirrer, cooler, spider and vacuum pump attached. The oil bath heated up to 130° C. When the reaction mixture was completely liquid the vacuum pump was turned on and the pressure was decreased to 40 mbar, this resulted instantly in distillation and fraction 1 could be collected when the overhead temperature was stable at 55° C. The distillation slowed down and stopped after 2 hours. In an attempt to remedy this the oil bath temperature was increased to 152° C. Pressure was also further decreased to 46 mbar but the overhead temperature remained at 35° C. and no distillation was observed and the reaction was stopped.

Figure 8:
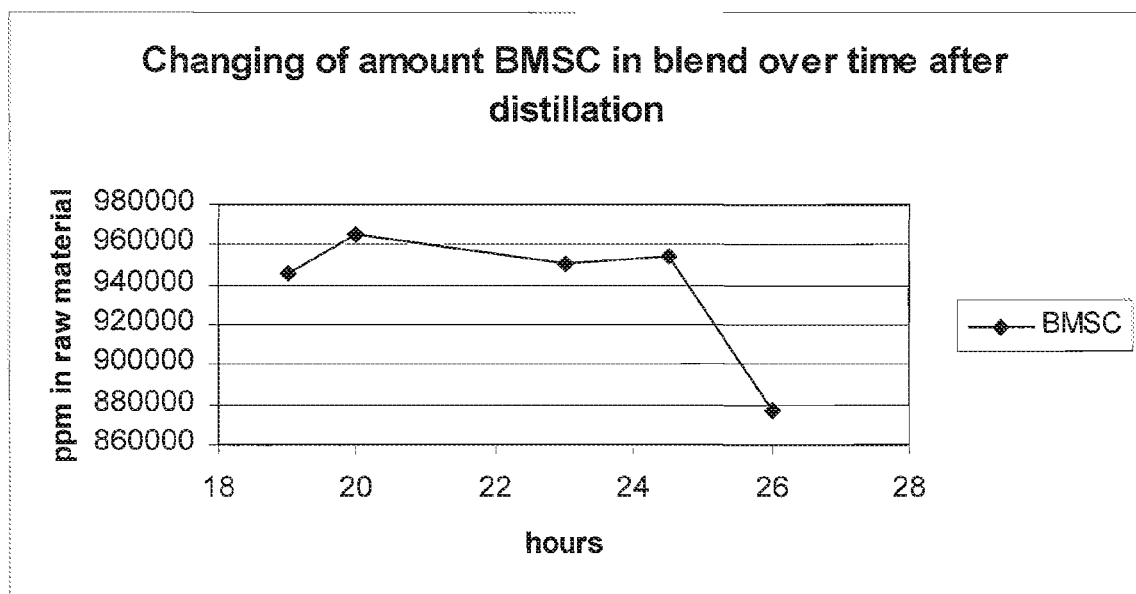
Figure 9:
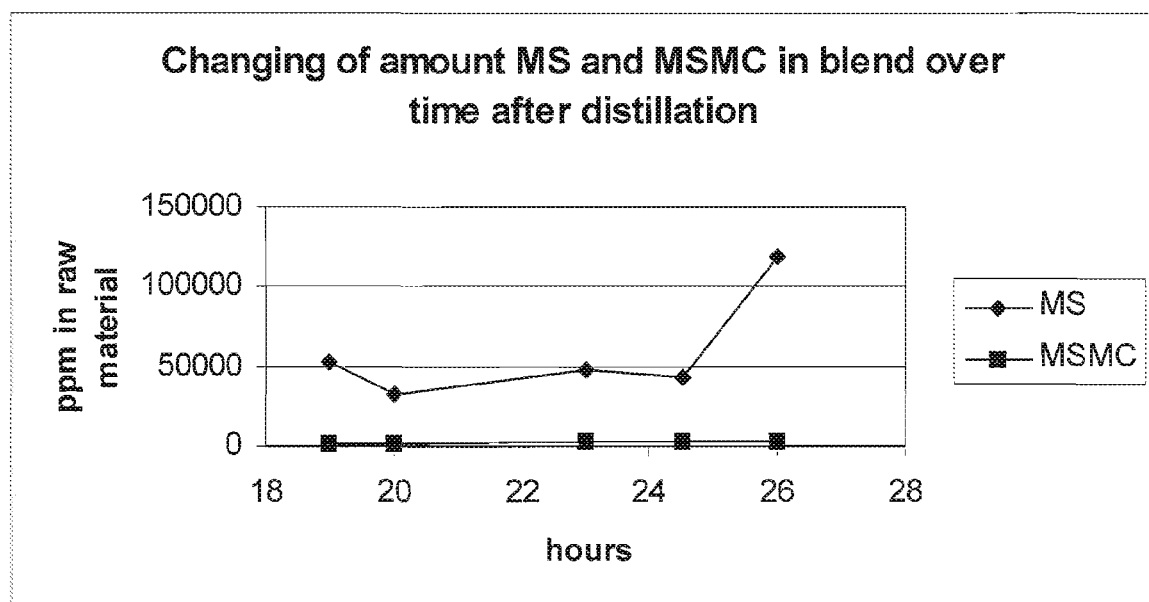

Reaction After Distillation:

In an attempt to get more towards a complete conversion the remaining mixture was left molten at 130° C. over night. After 19, 20 and 23 hrs sample 2, 3 and 4 respectively were taken. After 23 hrs, 10 ml NaOH 0.1M was added (under liquid level) with a syringe and the blend was again left to react. Samples were taken after 24.5 hrs and 26 hrs. HPLC results for these sample can be found in FIGS. 8 and 9. After distillation, the reaction stayed in equilibrium, after addition of an excess of the catalyst NaOH, reaction started again.

Working Example 7

Cracking BMSC Dissolved in DCM and Methanol with Catalyst

Figure 10:
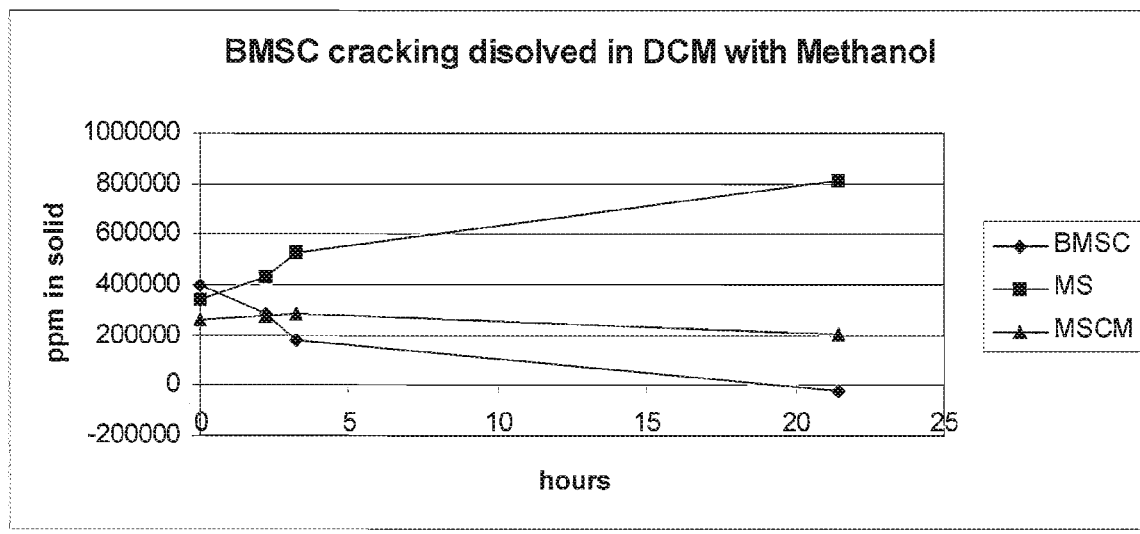

The reaction was done in a 500 ml round bottom flask with cooler and stirrer attached. 80.16 g BMSC was dissolved in 120 ml dichloromethane at 40° C. (oil bath set at 50° C.) under reflux. The solution became lucid when 10× more methanol was added compared to BMSC on molecular base (in this case that corresponds to 98 ml methanol). The oil bath was set at 55° C. and subsequently 800 l of catalyst (250 eq TMAH+100 eq NaOH) was added to the solution and kept under reflux at 43° C. This reaction mixture was left to react under reflux for 23 h and afterwards it was cooled down to RT. Samples were taken after 0, 2:25, 4.25 and 23 hrs. HPLC results of these sample are seen in FIG. 10.

Full or nearly full conversion was obtained. However the amount of MSMC increased significantly. It is apparent that the reaction takes much longer compared to the reaction in just methanol. Without being bound by a particular mechanism, the Inventors hypothesize that the amount of DCM decreased the probability that a BMSC molecule reacts with a MeOH causing the reaction to slow down.

Example 8

Cracking of BMSC in a Methanol Solution with 10 equ NaOH

Reaction:

The reaction was done in a 500 ml round bottom flask with cooler and stirrer attached. 20.23 g BMSC was dissolved in 400 ml Methanol at 65° C. (oil bath set at 85° C.) When all BMSC was dissolved 1 µl catalyst (10 eq NaOH) was added to the solution. This reaction mixture was left to react under reflux for 46:30 hrs. Afterwards the mixture was cooled down to RT. Samples were taken after 0, 1, 3, 5, 6:30, 23, 27, 27:30, 46:30 hrs.

Figure 11:
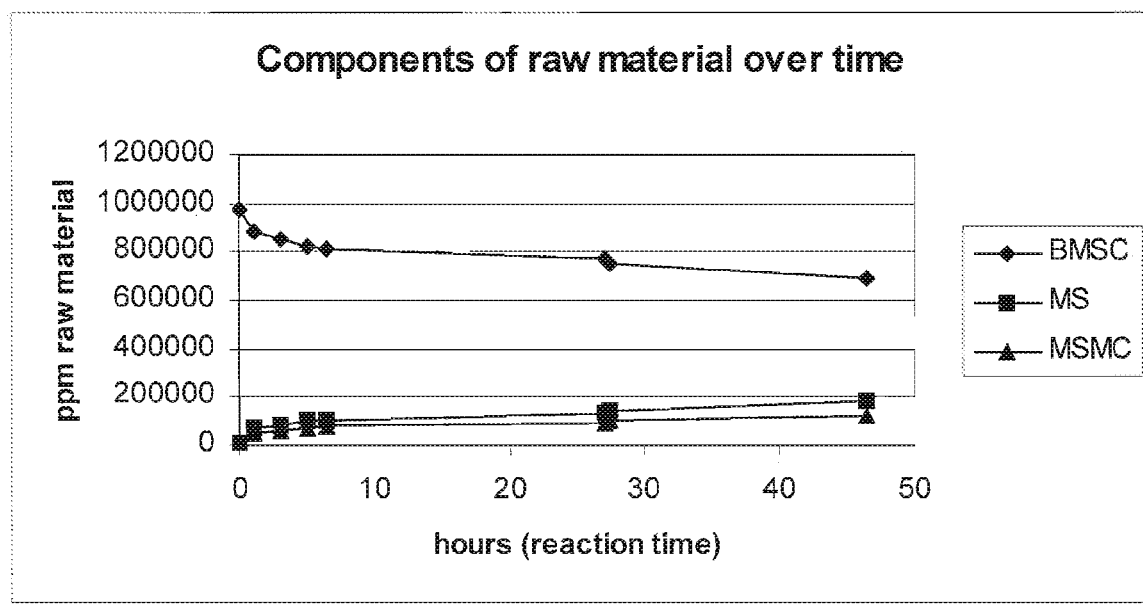

HPLC results of these samples are found in FIG. 11. The reaction occurred very slowly. After 46 hours only 40% conversion was obtained having almost 20% of the MSMC byproduct in the reaction mixture.

Discussion & Conclusion

The reactions that were done with BMSC in solution gave a high conversion rate whereas with the reaction in melt a much lower conversion was obtained. These results are summarized in the table 11 below:

TABLE 11

| Ex. | Melt/Solution | Final Conv. | Solvent | Catalyst | MSMC | Remark |
|---|---|---|---|---|---|---|
| 1 | Solution | 100% | MeOH | 250 uequ TMAH + 100 uequ NaOH | Low | Pure BMSC used |

TABLE 11-continued

| Ex. | Melt/Solution | Final Conv. | Solvent | Catalyst | MSMC | Remark |
|---|---|---|---|---|---|---|
| 2 | Melt | 6.45% | — | 250 uequ TMAH + 100 uequ NaOH | Low | Not enough water for reaction |
| 3 | Melt | 29.29% | — | 250 uequ TMAH + 100 uequ NaOH | Low | Stopped at equilibrium |
| 4 | Melt | 30% | — | 250 uequ TMAH + 100 uequ NaOH | Low | Stopped at equilibrium |
| 5 | Solution | 100% | MeOH | 250 uequ TMAH + 100 uequ NaOH | Low | Repeated WE 1 with BMSC Tar |
| 6 | Melt | 60% | — | 1505.9 uequ NaOH | Low | — |
| 7 | Solution | 100% | MeOH + DCM | 250 uequ TMAH + 100 uequ NaOH | High | — |
| 8 | Solution | 30% | MeOH | 10 uequ NaOH | High | No TMAH and less NaoH used |

The Examples start with pure BMSC dissolved in MeOH in the presence of catalyst in Example 1. The reaction was a success, also when it was repeated with actual BMSC tar in Example 5. Though some detectable levels of side products, MSMC (with HPLC UV detector), was found but these reacted away during the reaction. With Example 7 it was attempted to lower the amount of MeOH by dissolving BMSC first in DCM under reflux and then adding the MeOH in a second step. Unfortunately a lot of MSMC was formed during this reaction. Another approach was to minimize the amount of catalyst needed in the reaction this was tested in Example 8. The reaction was done with 10 meq NaOH instead of 100 meq, this reaction would eventually go to completion, however the reactivity was much lower thus the reaction took much more time. The challenge with these reactions with MeOH however was that only a 6% solution of BMSC in MeOH could be obtained under reflux. This means that when this reaction is scaled-up to a pilot plant or commercial plant vast amounts of solvents would be needed to perform this recycling step.

Next to the MeOH reactions trials were started with melt reactions in order to be able to leave out the solvents completely. This was done by starting with a melt mix of BMSC and an excess of catalyst. This reaction took place at 160° C. and full vacuum, to distill off the MS continuously. By doing that the reaction equilibrium is shifted towards the side of MS and thus towards complete conversion. Because the reaction was based on a reaction with water present it soon became clear that the conditions were too harsh for this type of reaction because at this temperature the water instantly devolitized and the reaction was stopped in Example 2. To solve this issue it was desired to add water continuously to the reaction blend in Example 3. However this was not an ideal situation because the water, when coming in to contact with the blend, reacted explosively since the temperature of the mix was far above the boiling point of water. Another disadvantage from this was that this effect would also cause the catalyst to stick on the walls and stop the reaction and potentially increase the hydrolysis reaction to form acid-substituted phenol from the ester-substituted phenol. In Example 4 this was validated by doing the reaction without continues distillation of the formed MS unfortunately the reaction equilibrated at 30% conversion. In example 6 a continuous addition of an excess of NaOH was performed to achieve a higher rate of conversion. This however did not give the desired effect. As a follow-up reaction for example 6, a distillation was carried out on the resulted material from Example 6, removing the MS would than push the equilibrium more towards completion/full conversion. When the MS was removed, the remaining blend was left to react again but after 4 hours still no reaction had occurred. Therefore an additional excess of NaOH was added to the blend and the reaction started again resulting in a 60% conversion.

The invention claimed is:

1. A method for producing an ester-substituted phenol product stream from an ester-substituted diaryl carbonate manufacturing waste stream, the method comprising the steps of:
   (1) obtaining a waste stream from an ester-substituted diaryl carbonate manufacturing facility, the waste stream comprising an ester-substituted diaryl carbonate,
   (2) creating a reaction mixture by combining the waste stream with a solvent selected from the group consisting of methanol, ethanol, n-propanol, iso-propanol, and water, and with a transesterification catalyst,
   (3) maintaining the reaction mixture at a reaction pressure at or below atmospheric pressure and at a reaction temperature for a period of time sufficient to produce ester-substituted phenol by solvolysis of the ester-substituted diaryl carbonate, and
   (4) removing the ester-substituted phenol in an ester-substituted phenol stream, wherein the solvent, the reaction temperature, and the reaction time are selected in combination such that less than 1,000 ppm of acid-substituted phenol is present in the ester-substituted phenol stream.

2. The method of claim 1, wherein the transesterification catalyst comprises sodium hydroxide.

3. The method of claim 2, wherein the transesterification catalyst further comprises tetramethyl ammonium hydroxide, tetramethyl phosphonium hydroxide, or both tetramethyl ammonium hydroxide and tetramethyl phosphonium hydroxide.

4. The method of claim 1, wherein the solvent, the reaction temperature, and the reaction time are selected in combination such that less than 100 ppm of acid-substituted phenol is present in the ester-substituted phenol stream.

5. The method of claim 4, wherein the solvent, the reaction temperature, and the reaction time are selected in combination such that less than 10 ppm of acid-substituted phenol is present in the ester-substituted phenol stream.

6. The method of claim 1, wherein the ester-substituted phenol is methyl salicylate, the ester-substituted diaryl carbonate is bismethylsalicylcarbonate, and the acid-substituted phenol is salicylic acid.

7. The method of claim 1, wherein the reaction mixture is maintained at a reaction temperature at or above the boiling point of the selected solvent at the reaction pressure, for a sufficient period of time to produce ester-substituted phenol from the ester-substituted diaryl carbonate, and wherein step (4) of removing an ester-substituted phenol gaseous product stream from the reaction mixture is performed continuously such that the reaction mixture comprises less than 1.0 wt. % ester-substituted phenol.

8. The method of claim 7, wherein step (4) of removing an ester-substituted phenol gaseous product stream from the reaction mixture is performed continuously such that the reaction mixture comprises less than 0.5 wt. % ester-substituted phenol.

9. The method of claim 7, wherein the reaction mixture is maintained at a reaction pressure of 0.8 bar or below and at a reaction temperature between 100° C. and 220° C.

10. The method of claim 1, wherein the solvent is selected from the group consisting of methanol, ethanol, n-propanol, and iso-propanol, wherein the reaction mixture comprises less than 1,000 ppm water, and wherein the reaction mixture is maintained at a reaction temperature below the atmospheric boiling point of the selected solvent.

11. The method of claim 10, wherein the reaction mixture further comprises water in an amount less than 500 ppm.

12. The method of claim 11, wherein the reaction mixture further comprises water in an amount less than 100 ppm.

13. The method of claim 10, wherein the reaction temperature is maintained at or below 70° C. and the reaction and reaction occurs for more than 1 hour.

14. The method of claim 12, wherein the reaction temperature is maintained in a range of at or between 50° C. and 65° C. and the reaction occurs for a period of time between 2 hours and 24 hours.

15. The method of claim 10, wherein the solvent in present in an amount corresponding to greater than 70 wt. % of the reaction mixture.

16. The method of claim 15, wherein the solvent is present in an amount corresponding to greater than 80 wt. % of the reaction mixture.

* * * * *

UNITED STATES PATENT AND TRADEMARK OFFICE
CERTIFICATE OF CORRECTION

PATENT NO. : 7,547,799 B1　　　　　　　　　　　　　　　　　　　　　　　Page 1 of 1
APPLICATION NO. : 12/143379
DATED : June 16, 2009
INVENTOR(S) : Belfadhel et al.

It is certified that error appears in the above-identified patent and that said Letters Patent is hereby corrected as shown below:

Column 30, Claim 13, Lines 5 through 7 should read: --The method of claim 10, wherein the reaction temperature is maintained at or below 70 °C and the reaction occurs for more than 1 hour.--

Column 30, Claim 15, Line 12 should read: --The method of claim 10, wherein the solvent is present--

Signed and Sealed this

Fourth Day of August, 2009

JOHN DOLL
*Acting Director of the United States Patent and Trademark Office*